(12) United States Patent
Fleury, Jr. et al.

(10) Patent No.: US 9,939,069 B2
(45) Date of Patent: *Apr. 10, 2018

(54) SENSOR-ENABLED GATE VALVE

(71) Applicant: Mueller International, LLC, Atlanta, GA (US)

(72) Inventors: Leo W. Fleury, Jr., N. Smithfield, RI (US); Normand James Roy, Coventry, RI (US); James Ola Williams, Malborough, MA (US); Kenneth A. Clark, Chattanooga, TN (US)

(73) Assignee: Mueller International, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/358,683

(22) Filed: Nov. 22, 2016

(65) Prior Publication Data

US 2017/0074408 A1   Mar. 16, 2017

Related U.S. Application Data

(60) Division of application No. 14/687,191, filed on Apr. 15, 2015, now Pat. No. 9,534,694, which is a
(Continued)

(51) Int. Cl.
*F16K 3/02* (2006.01)
*G01N 33/18* (2006.01)
(Continued)

(52) U.S. Cl.
CPC .............. *F16K 3/0209* (2013.01); *F16K 3/00* (2013.01); *F16K 3/30* (2013.01); *F16K 3/314* (2013.01);
(Continued)

(58) Field of Classification Search
CPC  G01N 33/18; F16K 3/316; F16K 3/30; F16K 3/00; F16K 3/0209; F16K 3/314; F16K 37/00; F16K 37/0091; F16K 27/044
(Continued)

(56) References Cited

U.S. PATENT DOCUMENTS 4,026,517 A   5/1977  Still
4,696,325 A   9/1987  Magee
(Continued)

FOREIGN PATENT DOCUMENTS

AU   2013215321   7/2017
CN   101900211    12/2010
(Continued)

OTHER PUBLICATIONS

Fleury, Leo W.; Office Action for Chinese Application Serial No. 201380018687.5, filed Jan. 30, 2013, dated Jul. 4, 2017, 7 pgs.
(Continued)

*Primary Examiner* — Daniel S Larkin
(74) *Attorney, Agent, or Firm* — Taylor English Duma LLP

(57) ABSTRACT

A gate valve includes a body, a stem, and a sensing bore. A subassembly includes a body, the body defining a sensing bore; and at least one of a vein and a plug in the sensing bore. A method of sensing an aspect of a water control system includes gaining access to the water control system through an access bore in a gate valve; at least temporarily removing water for testing from the access bore; and sensing an aspect of the removed water.

15 Claims, 18 Drawing Sheets

Related U.S. Application Data continuation of application No. 13/753,431, filed on Jan. 29, 2013, now Pat. No. 9,032,781.

(60) Provisional application No. 61/592,321, filed on Jan. 30, 2012, provisional application No. 61/643,400, filed on May 7, 2012.

(51) Int. Cl.

| F16K 37/00 | (2006.01) |
|---|---|
| F16K 31/50 | (2006.01) |
| F16K 3/314 | (2006.01) |
| F16K 27/04 | (2006.01) |
| F16K 3/00 | (2006.01) |
| F16K 3/30 | (2006.01) |
| F16K 3/316 | (2006.01) |

(52) U.S. Cl.
CPC ............ *F16K 3/316* (2013.01); *F16K 27/044* (2013.01); *F16K 31/504* (2013.01); *F16K 37/00* (2013.01); *F16K 37/0091* (2013.01); *G01N 33/18* (2013.01); *Y10T 137/8158* (2015.04)

(58) Field of Classification Search
USPC ................................ 73/53.01, 64.56, 863.86
See application file for complete search history.

(56) References Cited

U.S. PATENT DOCUMENTS

| 4,968,002 | A | 11/1990 | Gibson et al. |
| 5,056,758 | A | 10/1991 | Bramblet |
| 5,616,829 | A | 4/1997 | Balaschak et al. |
| 5,728,942 | A | 3/1998 | Boger |
| 6,240,789 | B1 | 6/2001 | Morlan et al. |
| 6,338,359 | B1 | 1/2002 | Welker |
| 6,557,577 | B1 | 5/2003 | Corte et al. |
| 6,698,444 | B1 | 3/2004 | Enston |
| 9,021,867 | B2 | 5/2015 | Fleury et al. |
| 9,032,781 | B2 | 5/2015 | Fleury |
| 9,534,694 | B2 | 1/2017 | Fleury, Jr. |
| 2013/0192348 | A1 | 8/2013 | Fleury |
| 2013/0192350 | A1 | 8/2013 | Fleury |

FOREIGN PATENT DOCUMENTS

| DE | 4328879 | 3/1995 |
| EP | 2809975 | 12/2016 |
| FR | 2764360 | 12/1998 |
| GB | 2511014 | 8/2014 |
| SG | 11201403056 R | 9/2016 |
| WO | 2013116276 | 8/2013 |

OTHER PUBLICATIONS

Fleury, Leo W.; Office Action for Mexico Application No. MX/a/2014/007571, filed Jan. 30, 2013, dated Jul. 26, 2017, 7 pgs.

Ray, Normand James; Supplementary Examination Report for Singapore application No. 10201505268W, filed Jan. 30, 2013, dated Aug. 23, 2017, 5 pgs.

Fleury, Leo W.; Office Action for Mexico Application No. MX/a/2014/007571, filed Jan. 30, 2013, dated Apr. 18, 2017, 4 pgs.

Fleury, Leo W.; Issue Notification for U.S. Appl. No. 13/753,428, filed Jan. 29, 2013, dated Apr. 15, 2015, 1 pg.

Fleury, Leo W.; Non-Final Office Action for U.S. Appl. No. 13/753,428, filed Jan. 29, 2013, dated Oct. 3, 2014, 17 pgs.

Fleury, Leo W.; Notice of Allowance for U.S. Appl. No. 13/753,428, filed Jan. 29, 2013, dated Jan. 6, 2015, 7 pgs.

Fleury, Leo W.; Corrected Notice of Allowability for U.S. Appl. No. 13/753,431, filed Jan. 29, 2013, dated Jan. 14, 2015, 4 pgs.

Fleury, Leo W.; Issue Notification for U.S. Appl. No. 13/753,431, filed Jan. 29, 2013, dated Apr. 29, 2015, 1 pg.

Fleury, Leo W.; Non-Final Office Action for U.S. Appl. No. 13/753,431, filed Jan. 29, 2013, dated Oct. 1, 2014, 12 pgs.

Fleury, Leo W.; Notice of Allowance for U.S. Appl. No. 13/753,431, filed Jan. 29, 2013, dated Jan. 5, 2015, 7 pgs.

Fleury Jr., Leo W.; Restriction Requirement for U.S. Appl. No. 14/687,181, filed Apr. 15, 2015, dated Apr. 8, 2016, 6 pgs.

Fleury, Jr., Leo W.; Notice of Allowance for U.S. Appl. No. 14/687,181, filed Apr. 15, 2015, dated Aug. 29, 2016, 5 pgs.

Fleury, Jr.; Leo W.; Corrected Notice of Allowability for U.S. Appl. No. 14/687,181, filed Apr. 15, 2015, dated Oct. 5, 2016, 4 pgs.

Fleury, Jr.; Leo W.; Non-Final Office Action for U.S. Appl. No. 14/687,181, filed Apr. 15, 2015, dated May 10, 2016, 19 pgs.

Fleury, Leo W.; Examination Report for Australian Patent Application No. 2013215321, filed Jan. 30, 2013, dated Aug. 29, 2016, 4 pgs.

Fleury, Leo W.; Office Action for Chinese application No. 201380018687.5, filed Jan. 30, 2013, dated Jan. 4, 2016, 19 pgs.

Fleury, Leo W.; Office Action for Chinese application No. 201380018687.5, filed Jan. 30, 2013, dated Jul. 5, 2016, 23 pgs.

Fleury Jr., Leo W.; Extended European Search Report for serial No. 13743385, filed Jan. 30, 2013, dated Sep. 22, 2015, 37 pgs.

Fleury, Leo W.; International Preliminary Report on Patentability for serial No. PCT/US2013/023755, filed Jan. 30, 2013, dated Aug. 14, 2014, 9 pgs.

Fleury, Leo W.; International Search Report and Written Opinion for serial No. PCT/US13/23755, filed Jan. 30, 2013, dated Apr. 5, 2013, 11 pgs.

Fleury, Leo W.; Examination Report for Singapore application No. 11201403056R, filed Jan. 30, 2013, dated Jul. 20, 2016, 10 pgs.

Fleury, Leo W.; Singapore Written Opinion for serial No. 11201403056R, filed Jan. 30, 20013, dated Jan. 26, 2016, 11 pgs.

Fleury, Leo W.; Singapore Written Opinion for serial No. 11201403056R, filed Jan. 30, 2013, dated Jul. 3, 2015, 11 pgs.

Fleury, Leo W.; U.S. Provisional Patent Application entitled: Sensor-Enabled Gate Valve having U.S. Appl. No. 61/592,321, filed Jan. 30, 2012, 27 pgs.

Fleury, Leo W.; U.S. Provisional Patent Application entitled: Sensor-Enabled Gate Valve having U.S. Appl. No. 61/643,400, filed May 7, 2012, 31 pgs.

Fleury, Jr., Leo W.; Issue Notification for U.S. Appl. No. 14/687,181, filed Apr. 15, 2015, dated Dec. 14, 2016, 1 pg.

Fleury, Jr., Leo W.; Office Action for Chinese application No. 201380018687.5, filed Jan. 30, 2013, dated Jan. 4, 2017, 15 pgs.

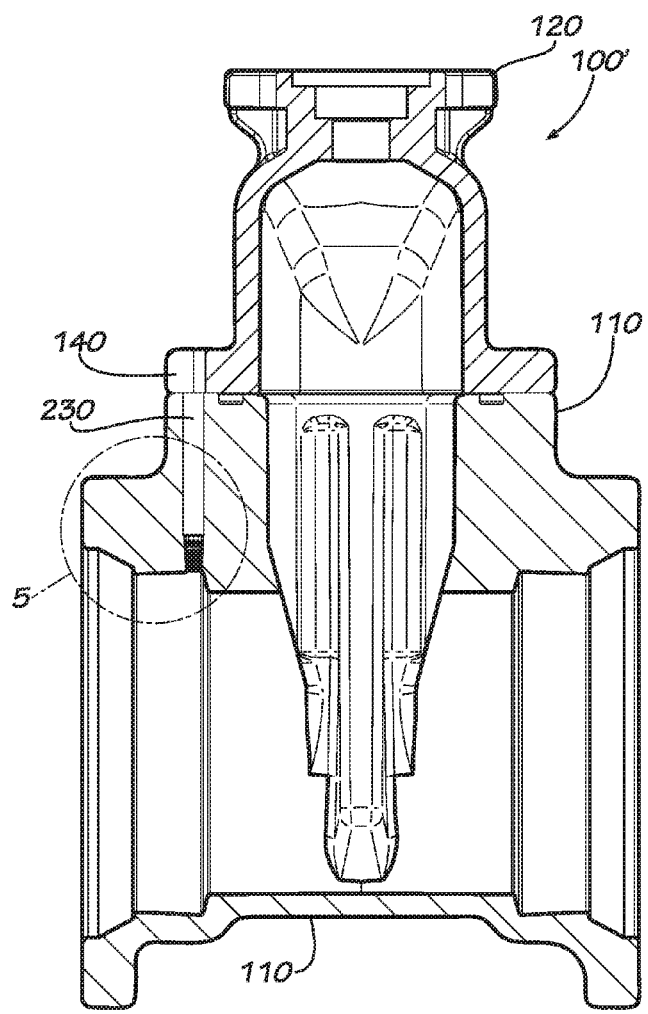
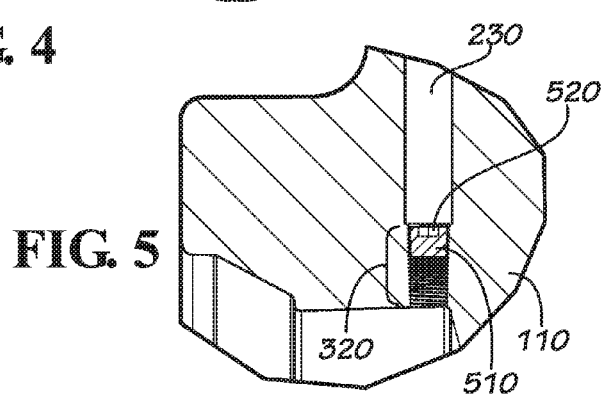
FIG. 4
FIG. 5

US 9,939,069 B2

SENSOR-ENABLED GATE VALVE

CROSS-REFERENCE TO RELATED APPLICATIONS

This application is a divisional of U.S. application Ser. No. 14/687,181, filed Apr. 15, 2015, which issued into U.S. Pat. No. 9,534,694, on Jan. 3, 2017, which is a continuation of U.S. application Ser. No. 13/753,431, filed Jan. 29, 2013, which issued into U.S. Pat. No. 9,032,781, on May 19, 2015, which claims the benefit of U.S. Provisional Application 61/592,321, filed on Jan. 30, 2012, and U.S. Provisional Application 61/643,400, filed on May 7, 2012, all of which are hereby incorporated by reference herein in their entireties.

FIELD

The current disclosure relates to valves. Particularly, the current disclosure relates to gate valves.

BACKGROUND

Valve elements are used to regulate or control the flow of material by opening, closing, or partially obstructing various passageways. One type of valve is a gate valve, which can be used in a number of applications.

SUMMARY

Disclosed is a gate valve including a body, a stem, and a sensing bore defined in the stem.

Also disclosed is a method of sensing an aspect of a water control system, the method including gaining access to the water control system through an access sensing bore defined in a stem of a gate valve; at least temporarily removing water for testing from the access sensing bore; and sensing an aspect of the removed water.

DESCRIPTION OF THE FIGURES

The features and components of the following figures are illustrated to emphasize the general principles of the present disclosure and are not necessarily drawn to scale. Corresponding features and components throughout the figures may be designated by matching reference characters for the sake of consistency and clarity. Although dimensions may be shown in some figures, such dimensions are exemplary only and are not intended to limit the disclosure.

FIG. 4 is a cross-sectional view of a subassembly of the body and the bonnet of FIG. 1 and a plug in accord with one embodiment of the current disclosure.

FIG. 5 is a view of the detail denoted by Detail 5 in FIG. 4.

DETAILED DESCRIPTION

Figure 1:
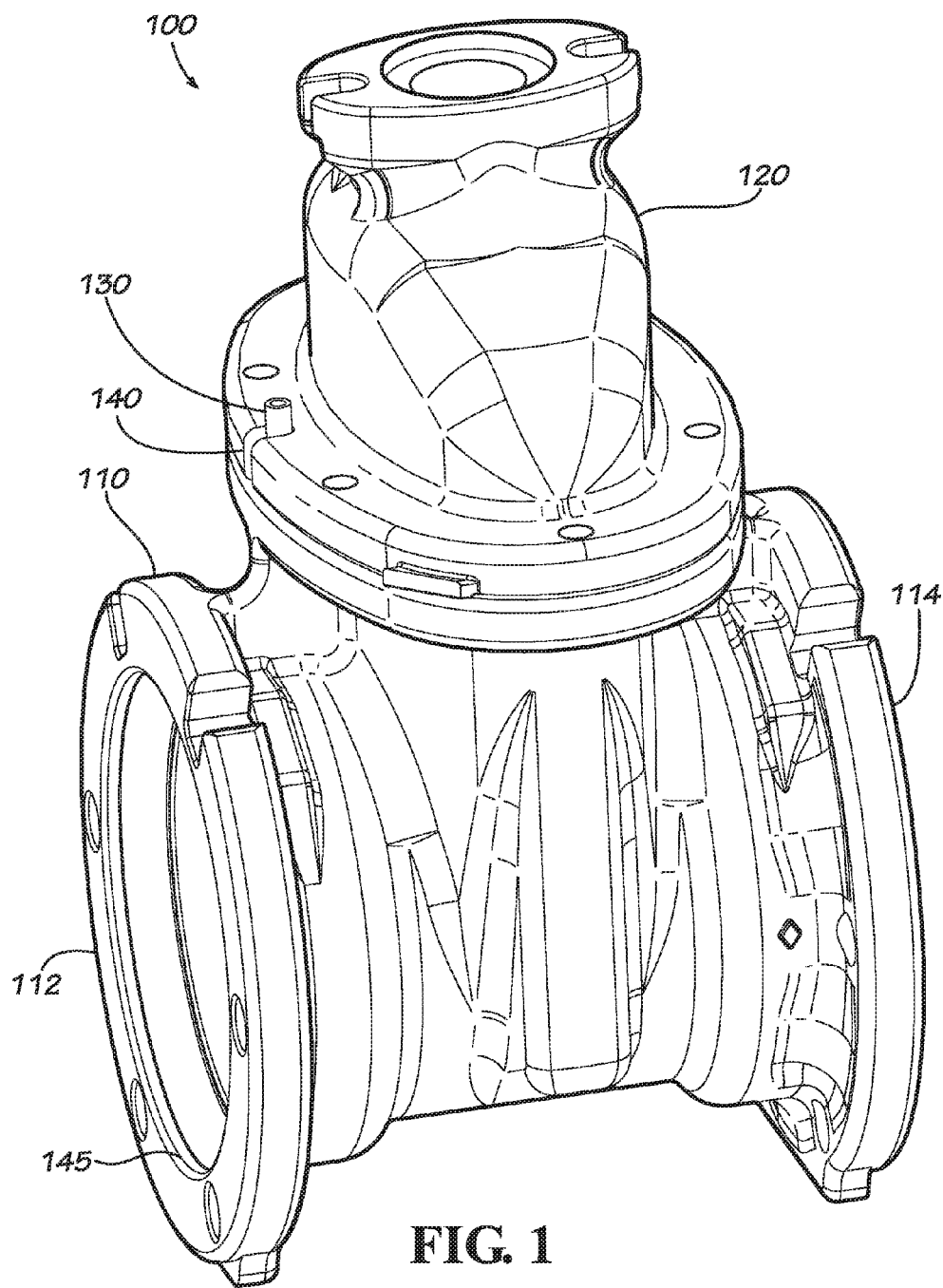
FIG. 1 is a perspective view of a subassembly of a body, a bonnet, and a vein in accord with one embodiment of the current disclosure.

Disclosed are methods, systems, and apparatus associated with sensing characteristics of fluid flow in a gate valve. A subassembly 100 of a body 110, a bonnet 120, and a vein 130 is seen in FIG. 1. The subassembly 100 is incorporated into a gate valve 1000, seen in FIG. 13A. The bonnet 120 includes a notch relief 140 into which the vein 130 fits. The body 110 defines a fluid bore 145 which is substantially continuous from an inlet end 112 to an outlet end 114 of the body 110 to allow fluid flow therein.

Figure 2:
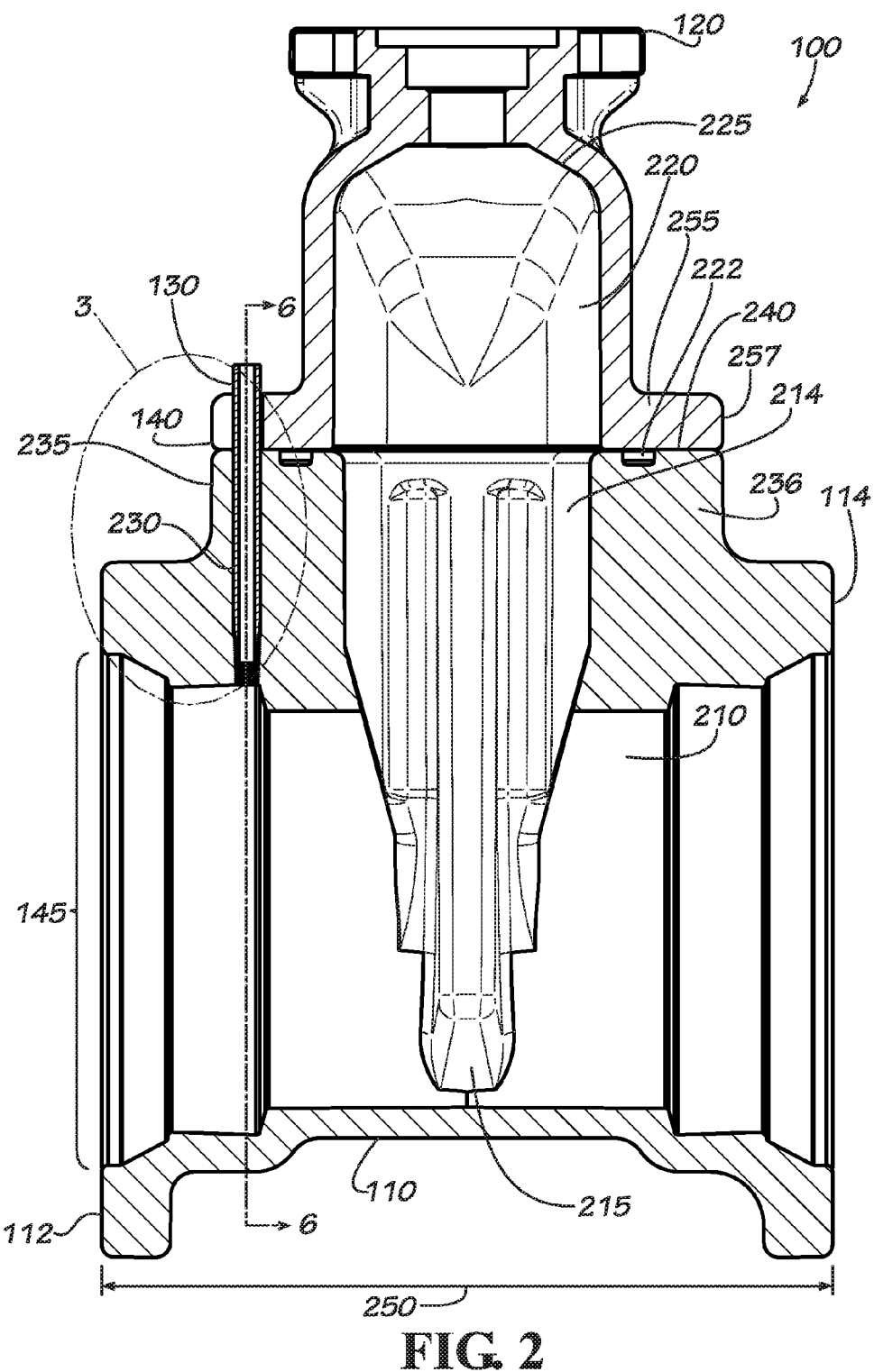
FIG. 2 is a cross-sectional view of the subassembly of FIG. 1.

As seen in cross-sectional view in FIG. 2, an interior 210 of the body 110 is substantially continuous and includes the fluid bore 145 and a valve cavity 214 that is defined within the body 110. The valve cavity 214 includes a valve seat 215. An interior 220 of the bonnet 120 is defined within a cavity 225 of the bonnet 120. The cavity 225 of the bonnet 120 is in fluid communication with the valve seat 215 which is then in fluid communication with the fluid bore 145. In use, fluid flows from the inlet 112 to the outlet 114. The gate valve 1000 incorporating the subassembly 100 includes an encapsulated disc 710 (see FIGS. 7A-7C) as a selective gate to prevent fluid flow. A gasket seat 222 provides space for inclusion of a gasket (not shown) to seal the connection between the bonnet 120 and the body 110. The bonnet 120 includes a flange 255 that matches up with the body 110 over the gasket seat 222, where a flange 655 (seen in FIG. 6)

matches that of the flange 255. The flange 255 allows for bolts to secure the bonnet 120 to the body 110. The flange 255 ends at an outermost extent 257. The flange 655 is readily discerned in FIG. 2 because the cross-sectional view is taken through webbing 235. Webbing 236 is seen on the body 110 one opposite side of the valve cavity 214 from webbing 235.

Also seen in FIG. 2, the notch 140 of the bonnet 120 aligns with a sensing bore 230 in the webbing 235 of the body 110. The sensing bore 230 extends from a flange end 240 of the body 110 down to the fluid bore 145. A lay length 250 as measured from the inlet end 112 to the outlet end 114 of the body 110 can also be seen.

Figure 3:
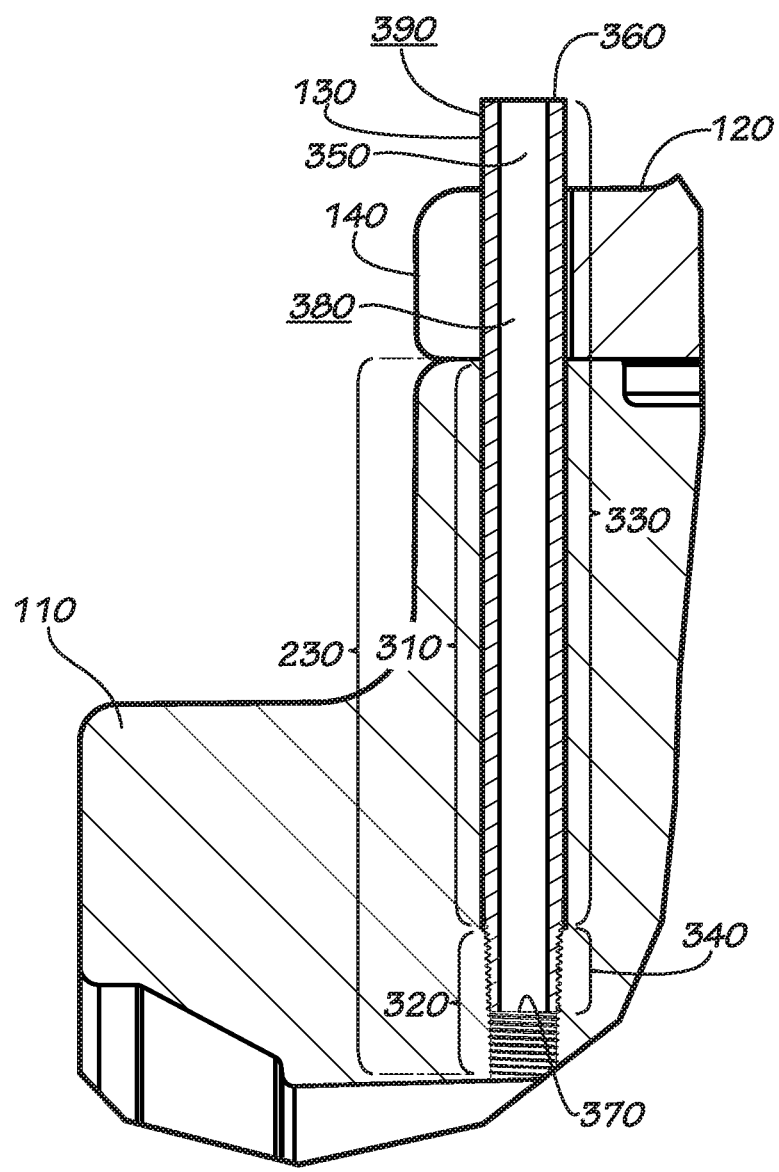
FIG. 3 is a view of the detail denoted by Detail 3 in FIG. 2.

As seen in FIG. 3, the sensing bore 230 includes an insert portion 310 and a threaded portion 320. Likewise, the vein 130 includes a shank portion 330 and a threaded portion 340. As can be seen, the vein 130 defines a bore 350 extending from a shank end 360 of the vein 130 to a thread end 370 of the vein 130 such that the bore 350 is continuous along the entire length of the vein 130. The vein 130 is shown with its threaded portion 340 engaging the threaded portion 320 of the sensing bore 230. This interaction secures the vein 130 in place and seals an interior surface 380 of the vein 130 from an exterior surface 390. Although the vein 130 and the sensing bore 230 are cylindrical in the current embodiment, these shapes should not be considered limiting on the scope of the disclosure.

As seen, the vein 130 extends nearly the entire length of the sensing bore 230. Although some unengaged threads are shown along the threaded portion 320, the vein 130 is designed to extend as far as possible into the sensing bore 230. The vein 130 is made of brass, stainless steel, copper, plastic, or any other type of material subject to low corrosion in an aqueous environment. Typically, the body 110 and the bonnet 120 are made of cast iron, although other similar materials may be used in various embodiments. Because cast iron can be highly corrosive when exposed to water, the extension of the vein 130 into the sensing bore 230 prevents corrosion, pitting, and tuberculation from degrading the ability of fluid to flow through the sensing bore 230. Typically, the body 110 will have a protective coating, but, in some circumstances, such a protective coating may not be applied easily to the interior of the sensing bore 230. However, in some embodiments, no vein 130 will be needed to prevent corrosion because a protective coating may be applied inside the sensing bore 230. In some embodiments, the vein 130 or another vein may be used but may not need to be extended along the entire length of the sensing bore 230.

As seen in FIGS. 1-3, the sensing bore 230 is generally cylindrical although the notch 140 is not. The notch 140 includes a portion that is semi-cylindrical, but the remainder of the notch 140 extends to the outermost extent 257. This configuration of the notch 140 allows for easier assembly of the bonnet 120 onto the body 110 if the vein 130 is already in place. For example, in some embodiments, the vein 130 may be prefabricated with the body 110 or may be preassembled with the body 110 as provided. For another example, in some embodiments, the subassembly 100 may need to be serviced or the bonnet 120 may need to be replaced due to cracking or other failure. Gate valves are designed in sizes ranging from a few inches to several feet in diameter. Particularly in embodiments with larger diameters, the bonnet 120 may be extremely heavy. Some gate valves are as large as 48-inches in diameter, and 24-inch diameter gate valves each include a bonnet weighing approximately 5,000 pounds. As such, attempting to align the vein 130 with a bore in the bonnet 120 may be very difficult. The notch 140 allows a user assembling the subassembly 100 to place the bonnet 120 onto the body 110 and then slide the bonnet 120 into place with the notch 140 aligned to the vein 130 and the sensing bore 230. However, in some embodiments—particularly in embodiments in which the bonnet 120 is relatively light—the bonnet 120 may include a bore instead of the notch 140 with an open side, as in the current embodiment.

One advantage to the placement of the sensing bore 230 and the vein 130 is that the placement does not require an increase in the lay length 250 of the body 110. Thus, the body 110 can be used with piping systems that are already designed for standard lay lengths such as lay length 250. From time to time, such gate valves will need servicing, either to remove blockages in the line, to repair cracked piping, to repair a non-functioning gate valve, or for other purposes. As such, damage to the vein 130 poses a significant risk. Another advantage to the placement of the vein 130 is that it is close to other components of the subassembly 100. As such, the vein 130 may be less-susceptible to movements in the earth whether such movements are seismic or due to assembly, disassembly, and burying of the subassembly 100 in the ground.

Another reason why it is advantageous to place the vein 130 on the subassembly 100 is that the subassembly 100 is part of the gate valve 1000. Pipes in a piping system are typically installed as quickly as possible. Gate valves such as gate valve 1000, on the other hand, are typically handled with care because improper installation of gate valves can lead to leaking piping systems and nonfunctioning gate valves. As such, there is a higher likelihood that sensors such as the pressure sensor—which may be relatively delicate and relatively expensive—are also handled with care if the vein 130 and the pressure sensor are attached to the gate valve 1000 as opposed to another component of the piping system.

As seen in the embodiments of FIGS. 4 and 5, a subassembly 100' may be substantially the same as subassembly 100. However, in some embodiments, the subassembly 100' may be provided with a plug 510 instead of the vein 130 as in subassembly 100. Such an embodiment as subassembly 100' may make the use of veins 130 optional. In such embodiments, one who assembles the piping system may optionally place the vein 130 or another device into the sensing bore 230 in place of the plug 510. The plug 510 is threaded to engage the threaded portion 320 of the sensing bore 230. As seen, the plug 510 includes a hex head 520 and operates similarly to a set screw in the current embodiment. However, in other embodiments, various configurations of plugs may be used. In some embodiments, a quick-connect adapter may be connected to the sensing bore 230 to allow quick assembly of sensing apparatus. In some embodiments, the vein 130 or a similar probe may be molded in place inside the body 110 casting. In such embodiments, threaded portions 320,340 may be unnecessary as compression from the cooling of the cast iron most likely will retain the vein 130 in place.

Figure 6:
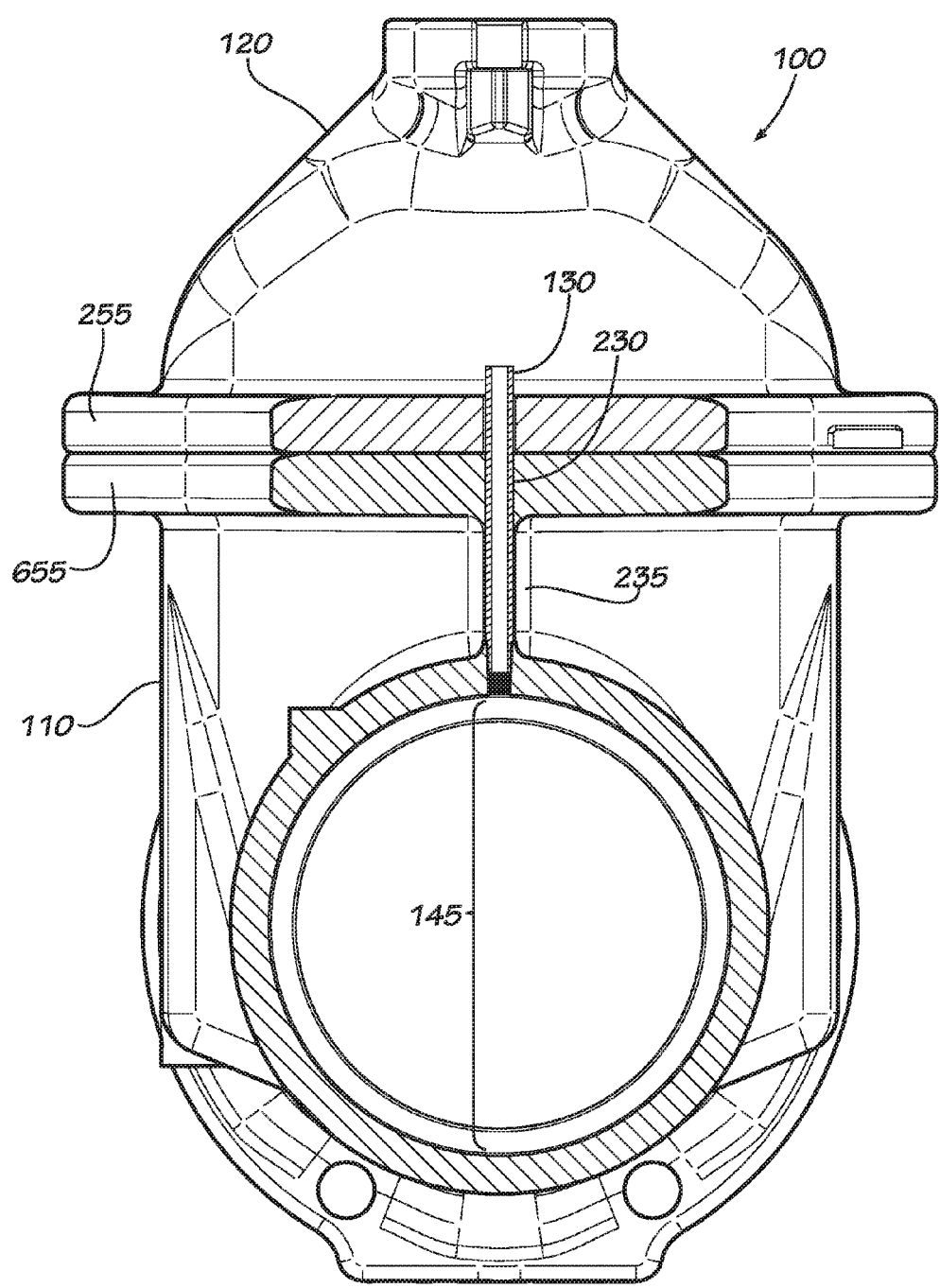
FIG. 6 is a cross-sectional view of the subassembly taken along the plane denoted by line 6 in FIG. 2.

FIG. 6 shows the subassembly 100 on a plane cut through the axis of the vein 130 orthogonal to the cutting plane in the view of FIG. 2. As can be seen, the flange 655 of the body 110 corresponds with the flange 255 of the bonnet 120. The thickness of the webbing 235 can be seen in the view. In various embodiments, the webbing 235 has various thicknesses. As shown, the subassembly 100 includes 6-inch fluid bore 145. The vein 130 is about one-half inch in external diameter. The webbing 235 (and also 236) is about one inch in thickness. As such, the sensing bore 230 is located centrally to retain the structural integrity of the webbing 235. In embodiments of larger size, the webbing 235 may be thicker even if the sensing bore 230 and the vein 130 are not. Thus, in larger size embodiments, placement of the sensing bore 230 is less important. In smaller size embodiments, a smaller vein 130 and sensing bore 230 may be used to accommodate thinner webbing 235.

Figure 7A:
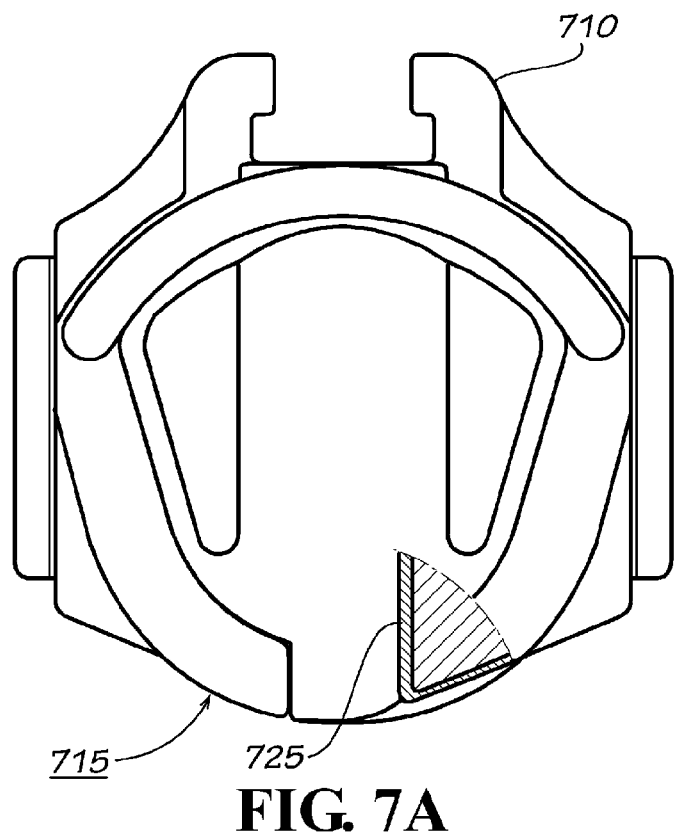
FIG. 7A is a front and partial cross-sectional view of an encapsulated disc for use with the subassembly of FIG. 1 in a gate valve.
Figure 7B:
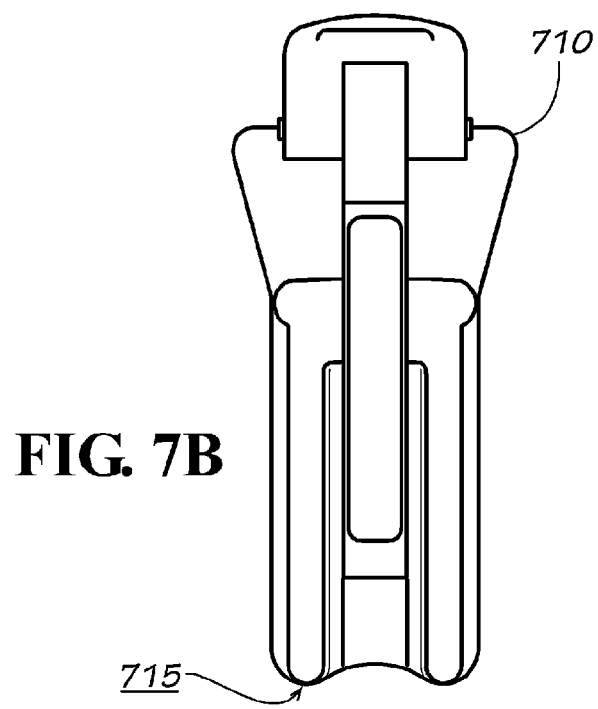
FIG. 7B is a side view of the encapsulated disc of FIG. 7A.
Figure 8B:
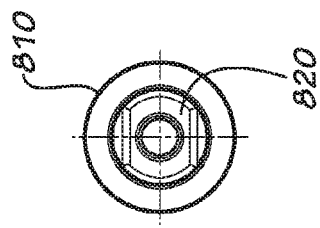
FIG. 8B is a top view of the stem of FIG. 8A.
Figure 7C:
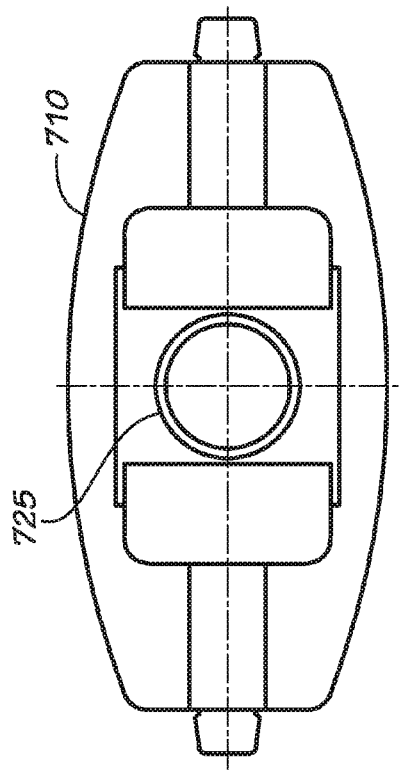
FIG. 7C is a top view of the encapsulated disc of FIG. 7A.
Figure 8A:
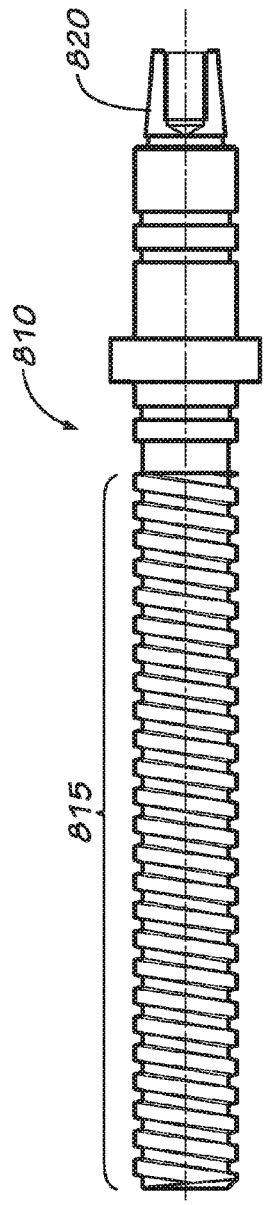
FIG. 8A is a side view of a stem for use with the subassembly of FIG. 1 in a gate valve.
Figure 9A:
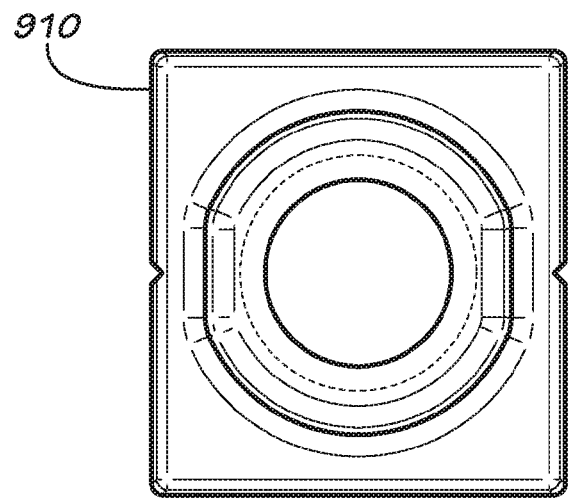
FIG. 9A is a top view of a disc nut for use with the subassembly of FIG. 1 in a gate valve.
Figure 9B:
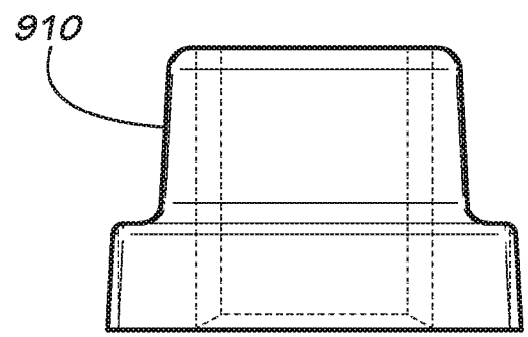
FIG. 9B is a front view of the disc nut of FIG. 9A.
Figure 9C:
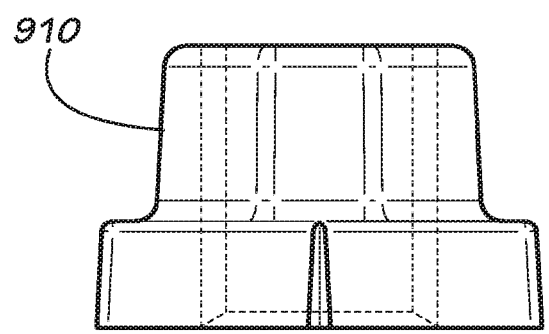
FIG. 9C is a side view of the disc nut of FIG. 9A.
Figure 10A:
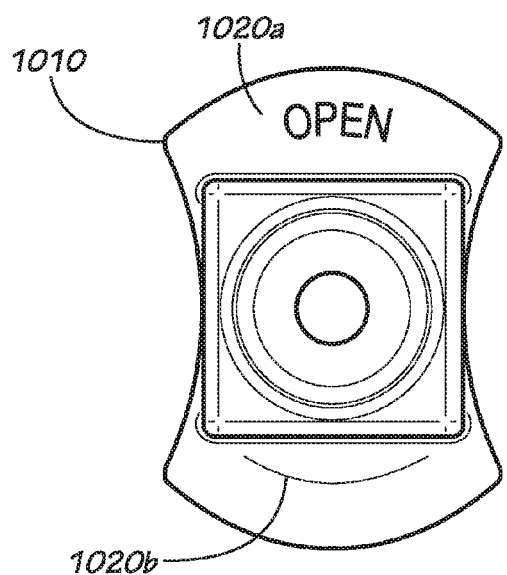
FIG. 10A is a top view of a disc nut for use with the subassembly of FIG. 1 in a gate valve.
Figure 10B:
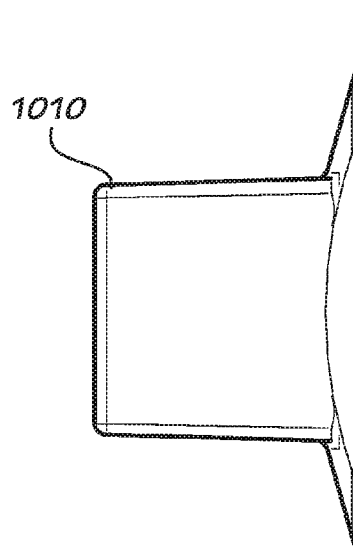
FIG. 10B is a side view of the disc nut of FIG. 10A.
Figure 10C:
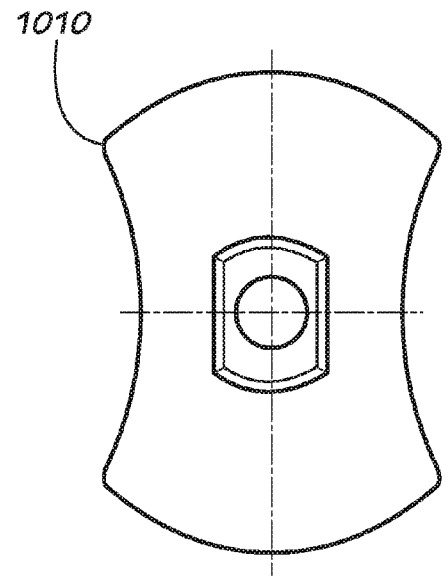
FIG. 10C is a bottom view of the disc nut of FIG. 10A.
Figure 11:
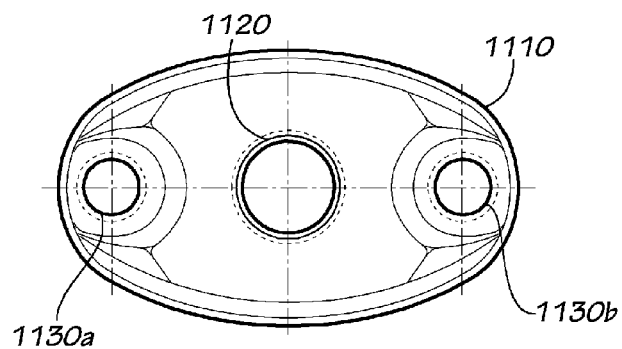
FIG. 11 is a top view of a top cover for use with the subassembly of FIG. 1 in a gate valve.
Figure 12:
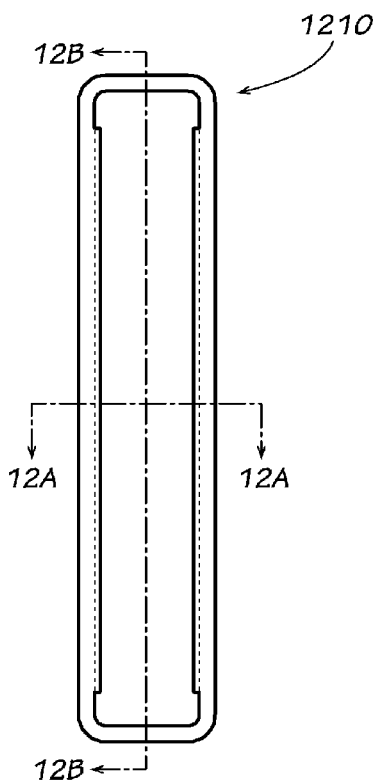
FIG. 12 is a side view of a guide cap for use with the subassembly of FIG. 1 in a gate valve.
Figure 12A:
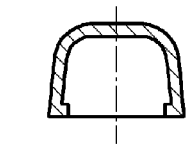
FIG. 12A a cross-sectional view of the guide cap taken in a plane indicated by line 12A in FIG. 12.
Figure 12B:
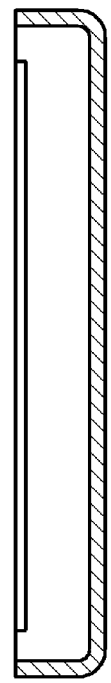
FIG. 12B a cross-sectional view of the guide cap taken in a plane indicated by line 12B in FIG. 12.

As seen in FIGS. 7A-7C, encapsulated disc 710 can be added to subassembly 100 as part of a gate valve 1000 in accord with one embodiment of the disclosure. As seen the encapsulated disc 710 includes a contact surface 715 for contacting and sealing with the valve seat 215 (seen in FIG. 2). The encapsulated disc 710 is coated in a water-impervious material that aids in sealing the gate valve 1000 when in the closed position. The encapsulated disc 710 includes an actuation bore 725. The encapsulated disc 710 is actuated by a stem 810 which is seen in FIGS. 8A and 8B. The stem 810 includes a threaded portion 815 that interacts with the actuation bore 725. The stem 810 also includes a nut portion 820 that can be rotated by the users to actuate the encapsulated disc 710 and to open or to close the gate valve 1000 selectively. FIGS. 9A-9C show various views of a disc nut 910 that couples the stem 810 and the encapsulated disc 710. FIGS. 10A-10C show various views of a wrench nut 1010 which includes indicators 1020a,b showing the direction of turning to place the gate valve 1000 in an open position. FIG. 11 shows a top cover 1110. The top cover 1110 includes an actuation bore 1120 and two connection bores 1130a,b. FIG. 12 shows a guide cap 1210. The guide cap 1210 is attached to the side of the encapsulated disc 710 to help prevent friction binding of the encapsulated disc 710 against the body 110. The guide cap 1210 is made of plastic in the current embodiment, although other similarly non-binding materials may be used in various embodiments. FIG. 12A shows a cross-sectional view of the guide cap taken in a plane indicated by line 12A in FIG. 12, and FIG. 12B shows a cross-sectional view of the guide cap taken in a plane indicated by line 12B in FIG. 12.

Figure 13A:
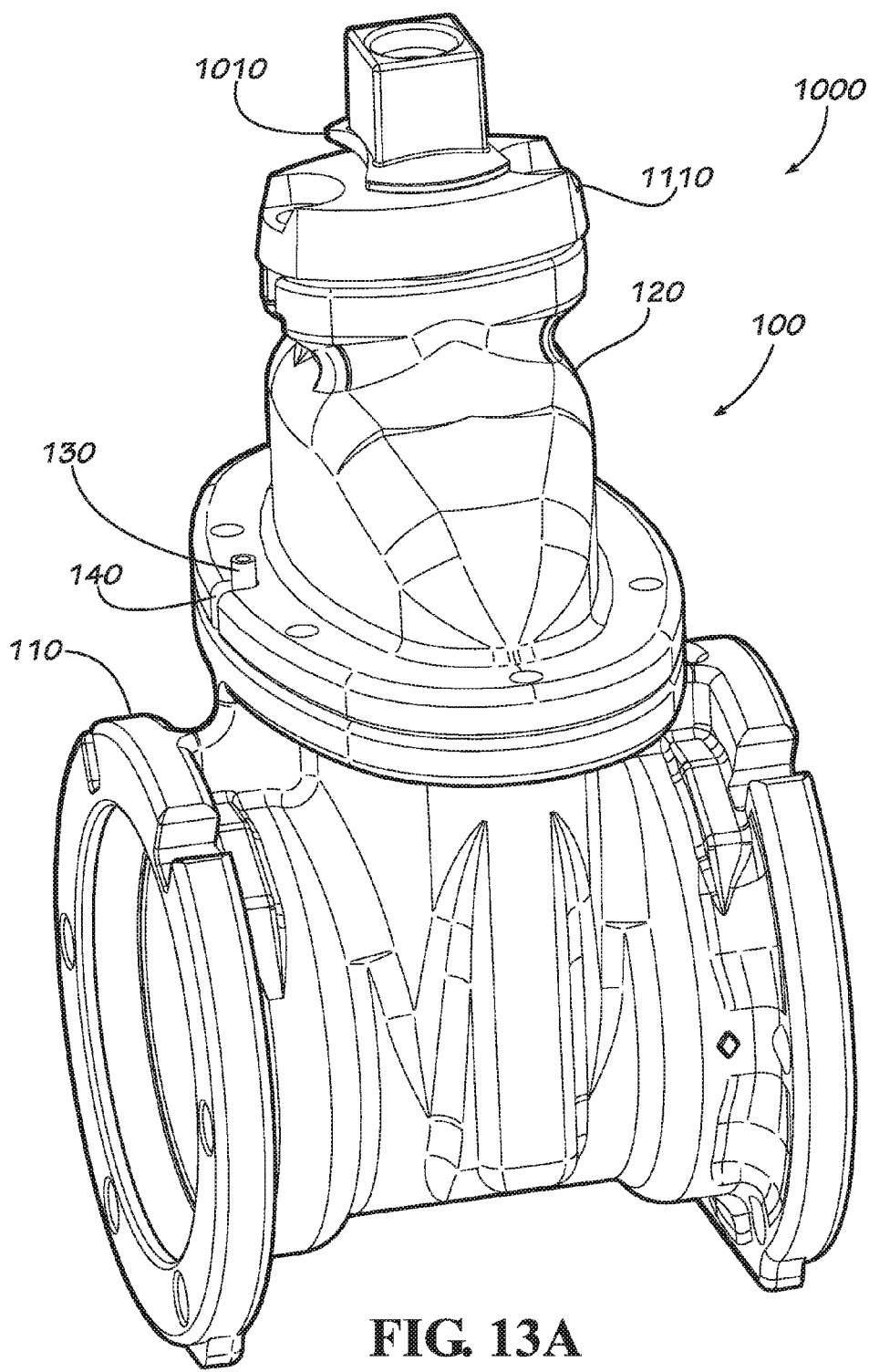
FIG. 13A is a perspective view of a gate valve in accord with one embodiment of the current disclosure including the subassembly of FIG. 1.
Figure 13B:
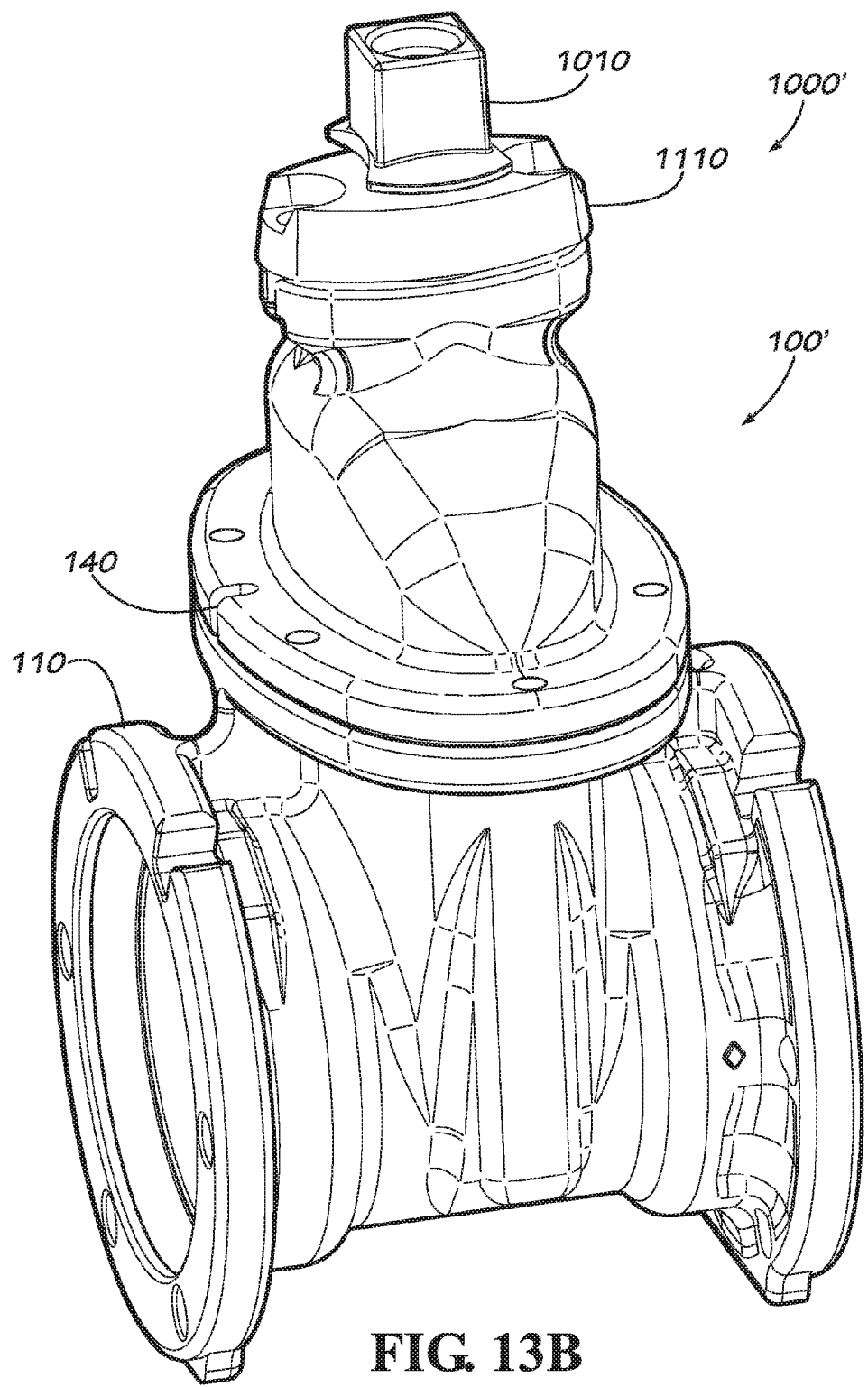
FIG. 13B is a perspective view of a gate valve in accord with one embodiment of the current disclosure including the subassembly of FIG. 4.
Figure 14:
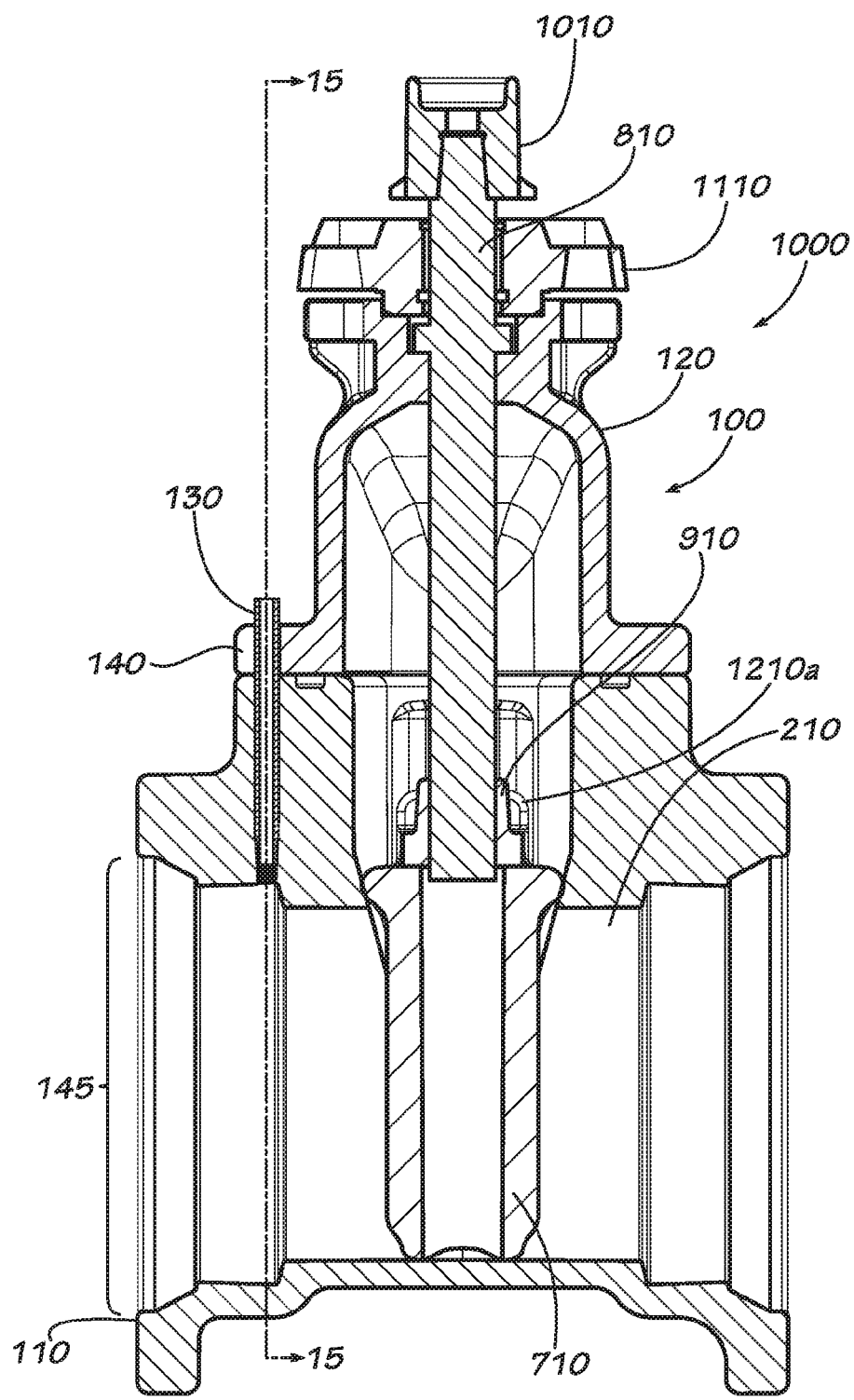
FIG. 14 is a cross-sectional view of the gate valve of FIG. 13A.
Figure 15:
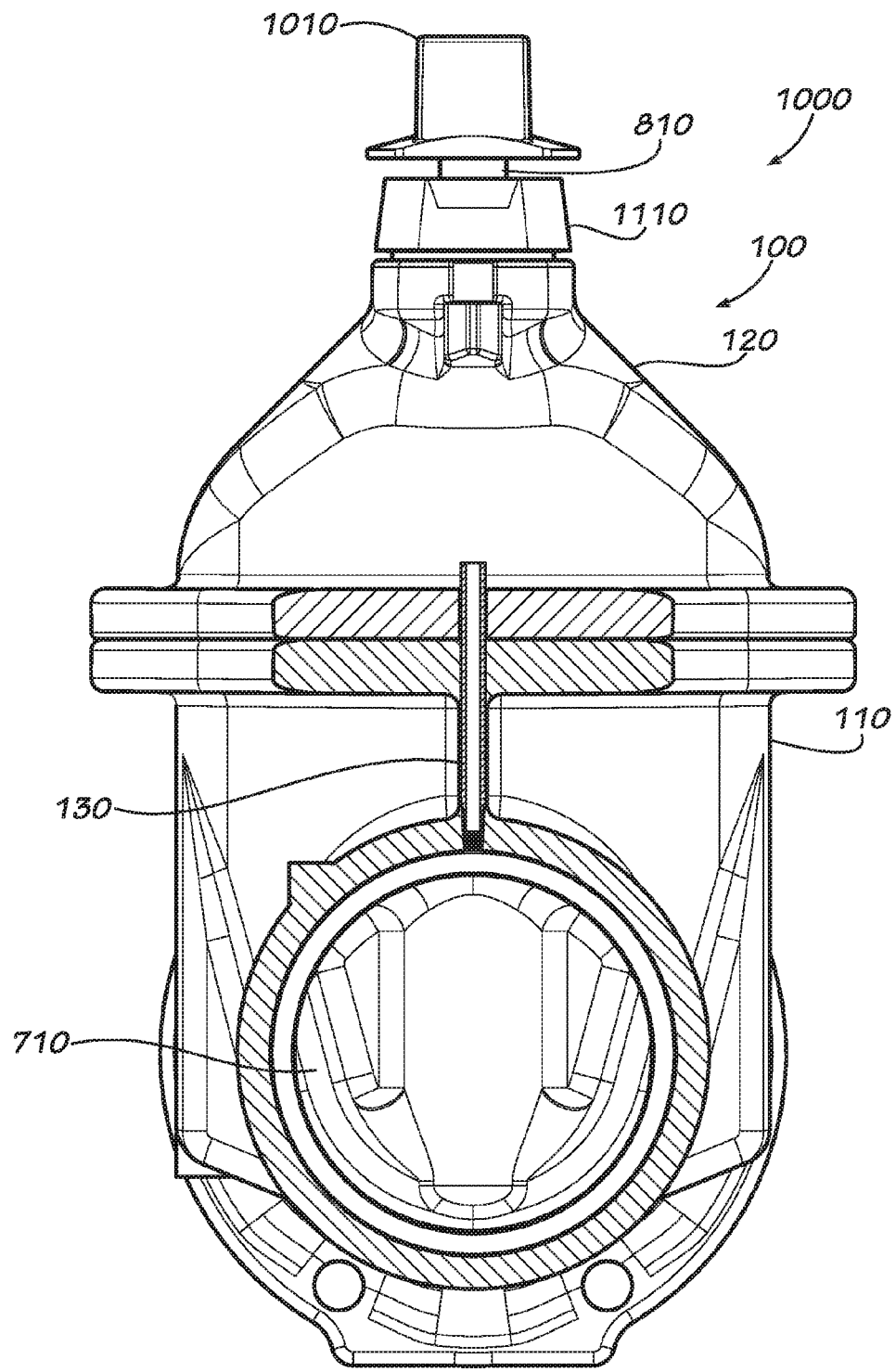
FIG. 15 is a cross-sectional view of the gate valve taken in a plane indicated by line 15 in FIG. 14.
Figure 16:
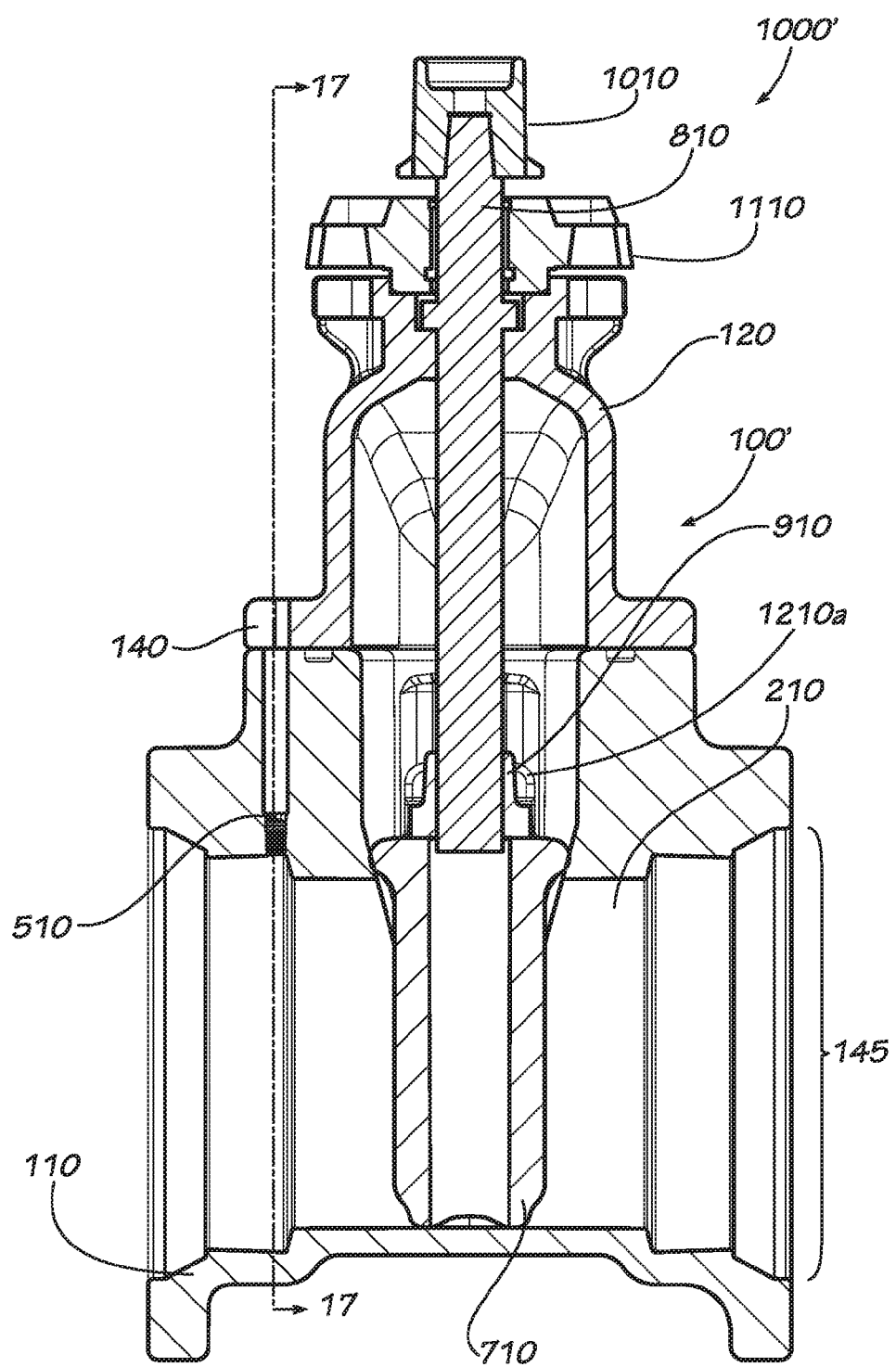
FIG. 16 is a cross-sectional view of the gate valve of FIG. 13B.
Figure 17:
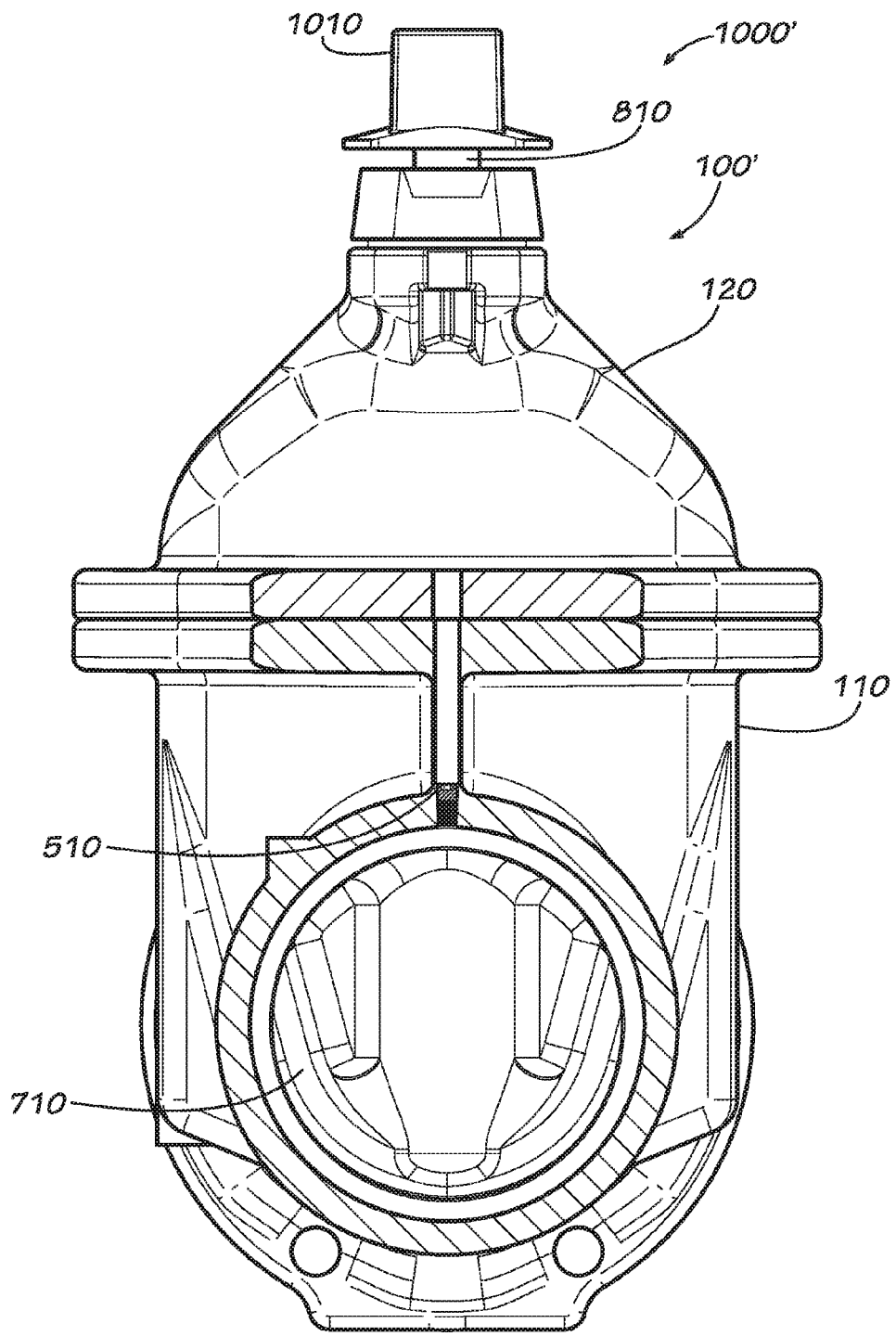
FIG. 17 is a cross-sectional view of the gate valve taken in a plane indicated by line 17 in FIG. 16.

Seen in FIG. 13A, a gate valve 1000 may incorporate the subassembly 100 along with the encapsulated disc 710 (not shown), the stem 810 (not shown), the disc nut 910 (not shown), the wrench nut 1010, the top cover 1110, and guide caps 1210a,b (not shown). As seen in FIG. 13B, a gate valve 1000' may include subassembly 100' as well. FIGS. 14 and 15 show cutaway views of the gate valve 1000. FIGS. 16 and 17 show cutaway views of the gate valve 1000'.

When in use, each gate valve 1000,1000' operates as its main function to allow a user selectively to prevent or to allow water flow through the fluid bore 145. Moving the encapsulated disc 710, the gate valve 1000,1000' can be sealed when the contact surface 715 is seated against the valve seat 215. Actuation of the stem 810 moves the encapsulated disc 710 out of the flow path of fluid, thereby opening the flow.

When the vein 130 is included, as in gate valve 1000, the sensing bore 230 and the bore 350 of the vein 130 provide a fluid pathway in fluid communication with the interior 210 of the body 110. Because fluid in a piping system is under pressure, fluid is forced through the fluid pathway, and pressure equalizes with the pressure inside the gate valve 1000. As such, a pressure sensor may be placed on the shank end 360 of the vein 130 to sense pressure within the piping system.

In other embodiments, other types of sensors may be connected to the vein 130 to sense other aspects of fluid in the system, including (particularly when the fluid is water) turbidity, chlorination, and acidity (pH), among others. In the current embodiment, the vein 130 allows sensors to be placed outside of the gate valve 1000, thereby providing a non-intrusive means of measuring aspects of the fluid in the piping system. However, some sensors may be placed proximate the thread end 370 of the vein 130 or, in some embodiments, may protrude inside the fluid bore 145. In particular, MEMS (microelectromechanical systems) sensors may be especially adapted for the small spaces of the bore 350.

It is common for gate valves such as gate valve 1000 to be buried six feet or more below the surface of the earth. In some embodiments, sensors such as the pressure sensor may be read electronically and may include wires leading to the surface. In some embodiments, the wires may be connected to a remote communicator such as an RF device. In some embodiments, the RF device will correspond with a mesh network. In those embodiments, it may be possible for the mesh network to measure pressure along different points in the piping system, thereby making easier determination of where leaks, blockages, or other failures in the piping systems may occur. Gate valve 1000' may be provided as a sensor-capable gate valve, such that the vein 130 is not included with the assembly but may be added by the user.

Another embodiment of a gate valve 2000 is shown and described with reference to FIG. 18. The gate valve 2000 includes the bonnet 120, the body 110, a stem 2810, and a top cover 2110, among other parts and features. As can be seen, the actuation bore 725 extends entirely through the encapsulated disc 710. When the gate valve 2000 is in an open position, the actuation bore 725 is in fluid communication with the interior of the body 110 and with fluid passing therethrough. As such, the actuation bore 725 can be used as testing port.

With the gate valves 1000,1000' of previously described embodiments, the sensing bore 230 is located in the webbing 235. Although possible, such a configuration introduces a machining operation to the casting process of the bonnet 120. Although it is also possible to cast the sensing bore 230, such a casting may be difficult to achieve. Moreover, the sensing bore 230 may weaken the webbing of the bonnet 120 in some applications, which may not be desirable. Further, because the bonnet 120 is made of cast iron, some steps are typically taken to ensure that the sensing bore 230 does not corrode (as previously described).

To address these concerns, the gate valve 2000 of the current embodiment includes a sensing bore 2230 machined into the stem 2810. The sensing bore 2230 is in fluid communication with the actuation bore 725 such that fluid in the body 110 can be communicated up the stem 2810 by fluid pressure in the system for testing.

Figure 19:
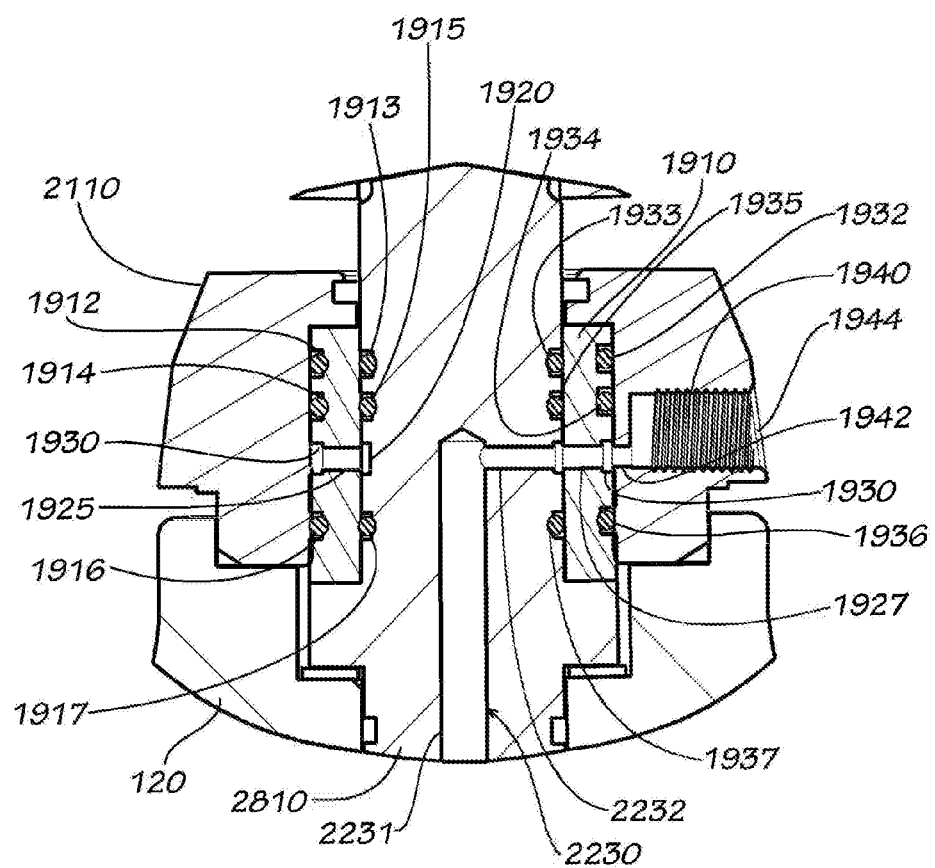
FIG. 19 is a detail view of the gate valve of FIG. 18.

Referring now to FIG. 19, a detail of the interaction of the stem 2810 with the top cover 2110 can be seen. As can be seen, the sensing bore 2230 includes an axial portion 2231 and a radial portion 2232. The radial portion 2232 provides a portion of the testing port from inside the stem 2810 to outside. Adjacent the stem 2810 between the top cover 2110 and the bonnet 120 is a bushing 1910. The bushing 1910 may be made of various materials including plastic, metal, and composites, among others. In the current embodiment, the bushing 1910 is annular, and many of the features as shown are annular as well.

The bushing 1910 of the current embodiment includes three annular gasket seating grooves 1912,1914,1916 into which gaskets 1932,1934,1936 seat to seal the testing port from leakage. The stem 2810 includes three annular gasket seating grooves 1913,1915,1917 that provide a sealing interface with gaskets 1933,1935,1937. In other embodiments, fewer or more gasket seating grooves may be included depending on sealing requirements. The number and configuration of gaskets and gasket seating grooves may change from one embodiment to another, as will be understood by one of skill in the art.

The radial portion 2232 communicates with an external shaft annulus 1920, which is an annulus groove defined in the bushing 1910. The external shaft annulus 1920 ensures that a line of fluid communication may be made regardless of the orientation of the stem 2810 with respect to the bushing 1910. The bushing 1910 includes two radial bores 1925,1927 that connect in fluid communication to the external shaft annulus 1920. The radial bores 1925,1927 are in fluid communication with an external bushing annulus 1930 which is similar to the external shaft annulus 1920 and substantially connects the two radial bores 1925,1927 along the outside of the bushing 1910.

As seen, the external bushing annulus 1930 communicates with an adapter bore 1940 in the top cover 2110. The adapter bore 1940 includes a neck portion 1942 and a threaded portion 1944 in the current embodiment, although the adapter bore 1940 need not include any specific connection configuration in all embodiments.

In the current embodiment, a sensing mechanism (not shown) may be connected to the adapter bore 1940 and in fluid communication with the interior of the gate valve 2000. As disclosed with respect to prior embodiments, the gate valve 2000 may include a plug (not shown) connected in the adapter bore 1940 if the testing port is not in use. For ease of reference, use of the testing port of the current embodiment includes the actuation bore 725, the sensing bore 2230, external shaft annulus 1920, the two radial bores 1925,1927, external bushing annulus 1930, and the adapter bore 1940. The gate valve 2000 may include the sensing mechanism connected in the adapter bore 1940. The gate valve 2000 may include a vein such as vein 130 of prior embodiments to connect to a sensing mechanism.

Locating the sensing bore 2230 in the stem 2810 addresses many of the concerns noted with respect to prior embodiments. Because the sensing bore 2230 is not defined in the bonnet 120, it does not require a machining operation in addition to casting. Moreover, the bonnet 120 is not weakened by the inclusion of sensing bore 230, which may be a concern in some embodiments. Further, because the stem 2810 is exposed to water throughout its life, it is typically made of a material that is substantially corrosion-resistant or subjected to a process to discourage corrosion. As such, no additional steps are required to protect the sensing bore 2230 from corrosion as would be required in prior embodiments. Further, the stem 2810 may be machined in some embodiments, and adding a machining step to include the sensing bore 2230 would not introduce excessive costs for additional machinery or capital into the process of manufacturing the stem 2810.

Figure 18:
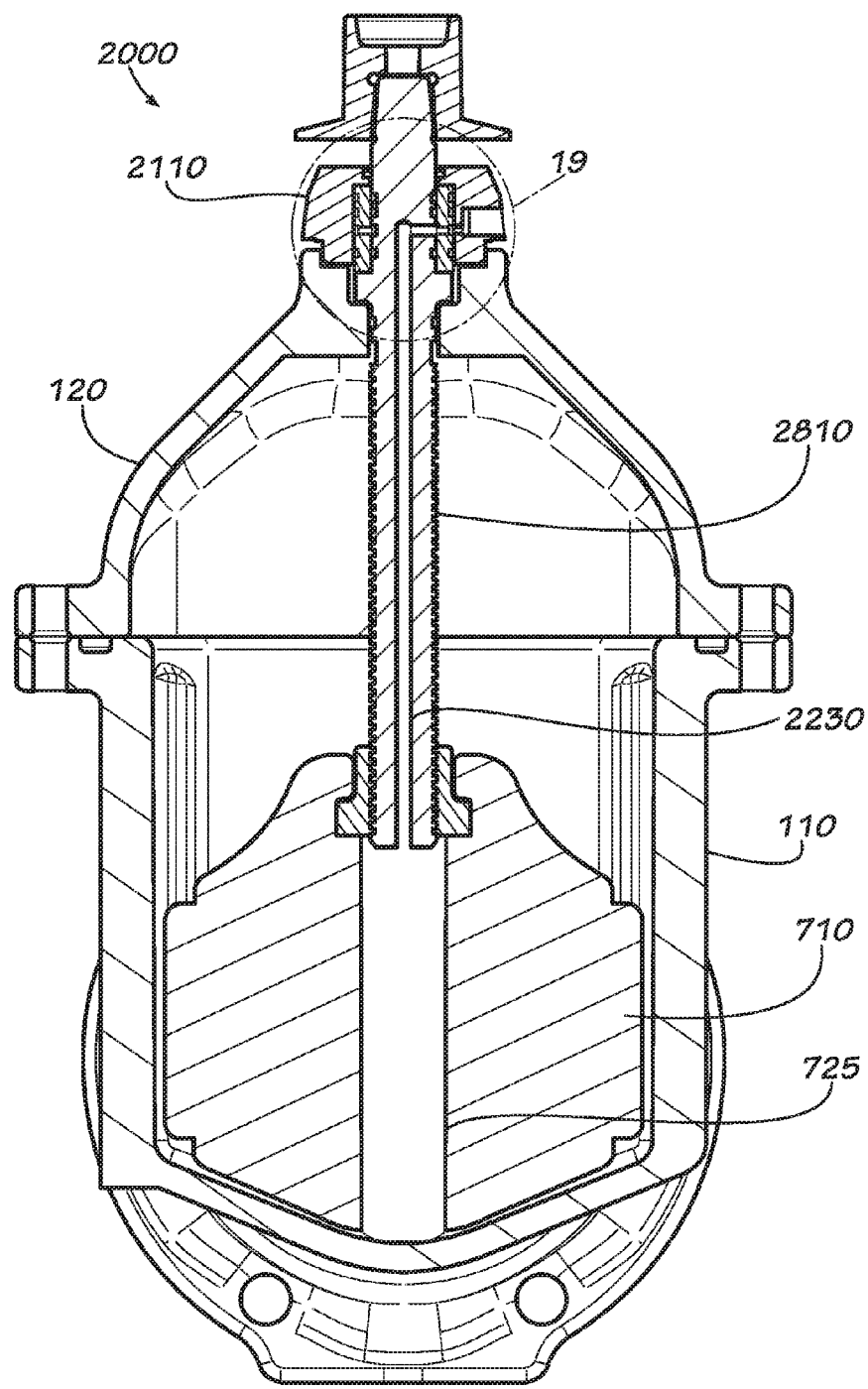
FIG. 18 is a cross-sectional view of a gate valve in accord with one embodiment of the current disclosure.

In operation, the gate valve 2000 is normally in an open position with the gate 710 raised (not shown in FIGS. 18 and 19). When the gate 710 is lifted, the actuation bore 725 is in fluid communication with the interior of the gate valve 2000, and, as such, is exposed to fluid pressure in the piping system. The fluid pressure in the piping system allows fluid flow into the axial portion 2231 of the sensing bore 2230 and then into the radial portion 2232. Fluid exits the radial portion 2232 and travels into the external shaft annulus 1920, into the two radial bores 1925,1927, into the external bushing annulus 1930, into the neck portion 1942 of the adapter bore 1940, and then into the threaded portion 1944 of the adapter bore 1940. The fluid in the threaded portion 1944 is then communicated into the sensing mechanism which may be capable of sensing various aspects of the fluid system, including pressure, turbidity, chlorination, and acidity (pH), among others.

In some conditions, the gate valve 2000 may be changed to a closed position. When the gate valve 2000 is in the closed position, the actuation bore 725 is not in fluid communication with the interior of the gate valve 2000. However, the gate valve 2000 should be in the closed position only when maintenance or faults are determined in the piping system, and, as such, use of the sensing mechanism may not be required when the gate valve 2000 is in the closed position. In other embodiments, the gate 710 may include a sensing bore (not shown) to communicate fluid from one side of the gate 710 into the actuation bore 725 and maintain the ability to test at least one part of the piping system when the gate valve 2000 is in the closed position.

It should be emphasized that the embodiments described herein are merely possible examples of implementations, merely set forth for a clear understanding of the principles of the present disclosure. Many variations and modifications may be made to the described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

One should note that conditional language, such as, among others, "can," "could," "might," or "may," unless specifically stated otherwise, or otherwise understood within the context as used, is generally intended to convey that certain embodiments include, while alternative embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

The invention claimed is:

1. A method of sensing an aspect of a water control system, the method comprising:
   gaining access to the water control system through an access bore in a gate valve;
   at least temporarily removing water for testing from the access bore; and
   sensing an aspect of the removed water;
   wherein the access bore is defined in a webbing of a body of the gate valve.

2. The method of claim 1, wherein the access bore extends from a flange end of the body to a fluid bore of the body.

3. The method of claim 1, wherein gaining access to the water control system through an access bore in the gate valve includes gaining access to the water control system through a vein extending through the access bore.

4. The method of claim 1, wherein the access bore is a sensing bore.

5. The method of claim 1, wherein the access bore is in fluid communication with a valve cavity defined by the gate valve.

6. The method of claim 1, further comprising sealing the access bore.

7. The method of claim 6, wherein sealing the access bore comprises installing a plug in the access bore.

8. A method of sensing an aspect of a water control system, the method comprising:
- gaining access to the water control system through an access bore in a gate valve;
- at least temporarily removing water for testing from the access bore; and
- sensing an aspect of the removed water;
- wherein gaining access to the water control system through an access bore in the gate valve includes gaining access to the water control system through a vein extending through the access bore.

9. The method of claim 8, wherein the access bore extends from a flange end of the body to a fluid bore of the body.

10. The method of claim 8, wherein the access bore is in fluid communication with a valve cavity defined by the gate valve.

11. The method of claim 8, further comprising sealing the access bore.

12. The method of claim 11, wherein sealing the access bore comprises installing a plug in the access bore.

13. A method of sensing an aspect of a water control system, the method comprising:
- gaining access to the water control system through an access bore in a gate valve;
- at least temporarily removing water for testing from the access bore; and
- sensing an aspect of the removed water;
- wherein gaining access to the water control system through an access bore in the gate valve includes gaining access to the water control system through an actuation bore defined by an encapsulated disc of the gate valve.

14. The method of claim 13, wherein the actuation bore is in fluid communication with a valve cavity defined by the gate valve.

15. The method of claim 13, further comprising gaining access to the water control system through a sensing bore defined by a stem of the gate valve, the sensing bore connected in fluid communication with the actuation bore.

* * * * *